US011687813B2

(12) United States Patent
Neumann (10) Patent No.: US 11,687,813 B2
(45) Date of Patent: Jun. 27, 2023

(54) SYSTEMS AND METHODS FOR RANKING ALIMENTARY COMBINATIONS USING MACHINE-LEARNING

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/000,998

(22) Filed: Aug. 24, 2020

(65) Prior Publication Data

US 2022/0058506 A1 Feb. 24, 2022

(51) Int. Cl.
*G06N 7/01* (2023.01)
*G06N 20/00* (2019.01)
*G16H 20/00* (2018.01)
*G16H 20/60* (2018.01)

(52) U.S. Cl.
CPC .............. *G06N 7/01* (2023.01); *G06N 20/00* (2019.01); *G16H 20/00* (2018.01); *G16H 20/60* (2018.01)

(58) Field of Classification Search
None
See application file for complete search history.

(56) References Cited

U.S. PATENT DOCUMENTS 6,980,999 B1 12/2005 Grana
8,920,175 B2 12/2014 Black et al.
10,360,495 B2 7/2019 Chapela et al.
(Continued)

FOREIGN PATENT DOCUMENTS

JP        4589580 B2 * 12/2010
WO    WO2016065463      5/2016
WO    WO2020115362      6/2020

OTHER PUBLICATIONS

Chenarides, Lauren. "Essays on the Economics of Food Availability and Food Deserts." Order No. 28213072 The Pennsylvania State University, 2017. Ann Arbor: ProQuest. Web. Feb. 1, 2023. (Year: 2017).*

(Continued)

*Primary Examiner* — Lena Najarian
(74) *Attorney, Agent, or Firm* — Caldwell Intellectual Property Law (57) ABSTRACT

A system for ranking alimentary combinations includes a computing device configured to provide a nutrient instruction set including a plurality of target nutrient quantities corresponding to a plurality of candidate alimentary combinations, determine a per-combination alimentary instruction set as a function of the plurality of target nutrient quantities, receive, from each alimentary provider device of a plurality of alimentary provider devices, a plurality of provider ingredient combinations, generate a ranked list of alimentary combinations as a function of the plurality of provider alimentary combinations, receive a user selection of a candidate alimentary combination corresponding to an edible of the plurality of candidate alimentary combinations, and generate a modified ranked list of alimentary combinations as a function of the user selection and the nutrient instruction set.

18 Claims, 6 Drawing Sheets

(56) References Cited

U.S. PATENT DOCUMENTS

| | | | |
|---|---|---|---|
| 2012/0083669 A1* | 4/2012 | Abujbara | G16H 20/60 |
| | | | 600/300 |
| 2014/0255882 A1 | 9/2014 | Hadad et al. | |
| 2015/0161910 A1 | 6/2015 | Bailor | |
| 2015/0216413 A1* | 8/2015 | Soyao | G16H 10/60 |
| | | | 709/204 |
| 2016/0364548 A1 | 12/2016 | Springer | |
| 2017/0116661 A1* | 4/2017 | Sundaram | G06Q 30/0633 |
| 2018/0144820 A1 | 5/2018 | Grimmer et al. | |
| 2018/0165732 A1* | 6/2018 | Ezra | G06Q 10/06 |
| 2018/0233064 A1 | 8/2018 | Dunn et al. | |
| 2018/0240359 A1* | 8/2018 | Hujsak | G06N 5/022 |
| 2018/0293638 A1 | 10/2018 | Simpson | |
| 2019/0073601 A1* | 3/2019 | Alkan | G06N 20/00 |

OTHER PUBLICATIONS https://www.ncbi.nlm.nih.gov/pmc/articles/PMC5579706/pdf/nutrients-09-00913.pdf.

https://www.researchgate.net/publication/334529528_A_food_recommender_system_considering_nutritional_information_and_user_preferences (via 'Download full-text PDF' link).

https://www.researchgate.net/profile/Luis_Rita2/publication/340133854_Machine_Learning_for_Building_a_Food_Recommendation_System/links/5e7aa059a6fdcc57b7bbaf10/Machine-Learning-for-Building-a-Food-Recommendation-System.pdf.

\* cited by examiner

SYSTEMS AND METHODS FOR RANKING ALIMENTARY COMBINATIONS USING MACHINE-LEARNING

FIELD OF THE INVENTION

The present invention generally relates to the field of network communication and processing. In particular, the present invention is directed to systems and methods for ranking alimentary combinations using machine learning

BACKGROUND

Current alimentary design systems do not optimize the nutritional delivery based on the physiological state of an individual. This leads to an inefficient nutrition delivery system and a poor delivery model. The current invention disclosed provides an optimized nutrient delivery system through a machine-learning process to aid in ameliorating user afflictions.

SUMMARY OF THE DISCLOSURE

In an aspect, a system for ranking alimentary combinations using machine learning includes a computing device configured to provide a nutrient instruction set including a plurality of target nutrient quantities corresponding to a plurality of afflictions, determine a per-combination alimentary instruction set as a function of the plurality of target nutrient quantities, receive, from each alimentary provider device of a plurality of alimentary provider device, a plurality of provider alimentary combinations, generate a ranked list of alimentary combinations as a function of the plurality of provider alimentary combinations, wherein generating includes determining a nutrient listing corresponding to each provider ingredient combination of the plurality of provider ingredient combinations, calculating a distance from the nutrient listing to the per-combination alimentary instruction set, and selecting at least an ingredient listing that minimizes the distance, and ranking the plurality provider alimentary combinations to minimize the distance, receive a user affliction target of a provider alimentary combinations corresponding to a meal of the plurality of meal combinations, and generate a modified ranked list of alimentary combinations as a function of the user affliction and the nutrient instruction set.

In another aspect, a method of ranking alimentary combinations using machine learning includes providing, by a computing device, a nutrient instruction set including a plurality of target nutrient quantities corresponding to a plurality of afflictions. The method includes determining, by the computing device, a per-combination alimentary instruction set as a function of the plurality of target nutrient quantities. The method includes receiving, by the computing device, from each alimentary provider device of a plurality of alimentary provider device, a plurality of provider alimentary combinations. The method includes generating, by the computing device, a ranked list of alimentary combinations as a function of the plurality of provider alimentary combinations, wherein generating includes determining a nutrient listing corresponding to each ingredient combination of the plurality of provider alimentary combinations, calculating a distance from the nutrient listing to the per-combination alimentary instruction set, and selecting at least an ingredient listing that minimizes the distance, and ranking the plurality provider alimentary combinations to minimize the distance. The method includes receiving, by the computing device, a user nutrient instruction set of a per-combination alimentary instruction set corresponding to a meal of the plurality of meal combinations. The method includes generating, by the computing device, a modified ranked list of alimentary combinations as a function of the user affliction and the nutrient instruction set.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for ranking alimentary combinations using machine learning. In an embodiment, this system provides an alimentary combination for a plurality of user afflictions as a function of the target nutrient quantities required. Target nutrient quantities may include recommendations based on user affliction. In an embodiment this system can be used to guide a user in the selection of an alimentary combination instruction set. Aspects of the present disclosure allow for alimentary combinations that may aid in amelioration of a user affliction due to target nutrients being delivered. Exemplary embodiments illustrating aspects of the present disclosure are described below in the context of several specific examples.

Figure 1:
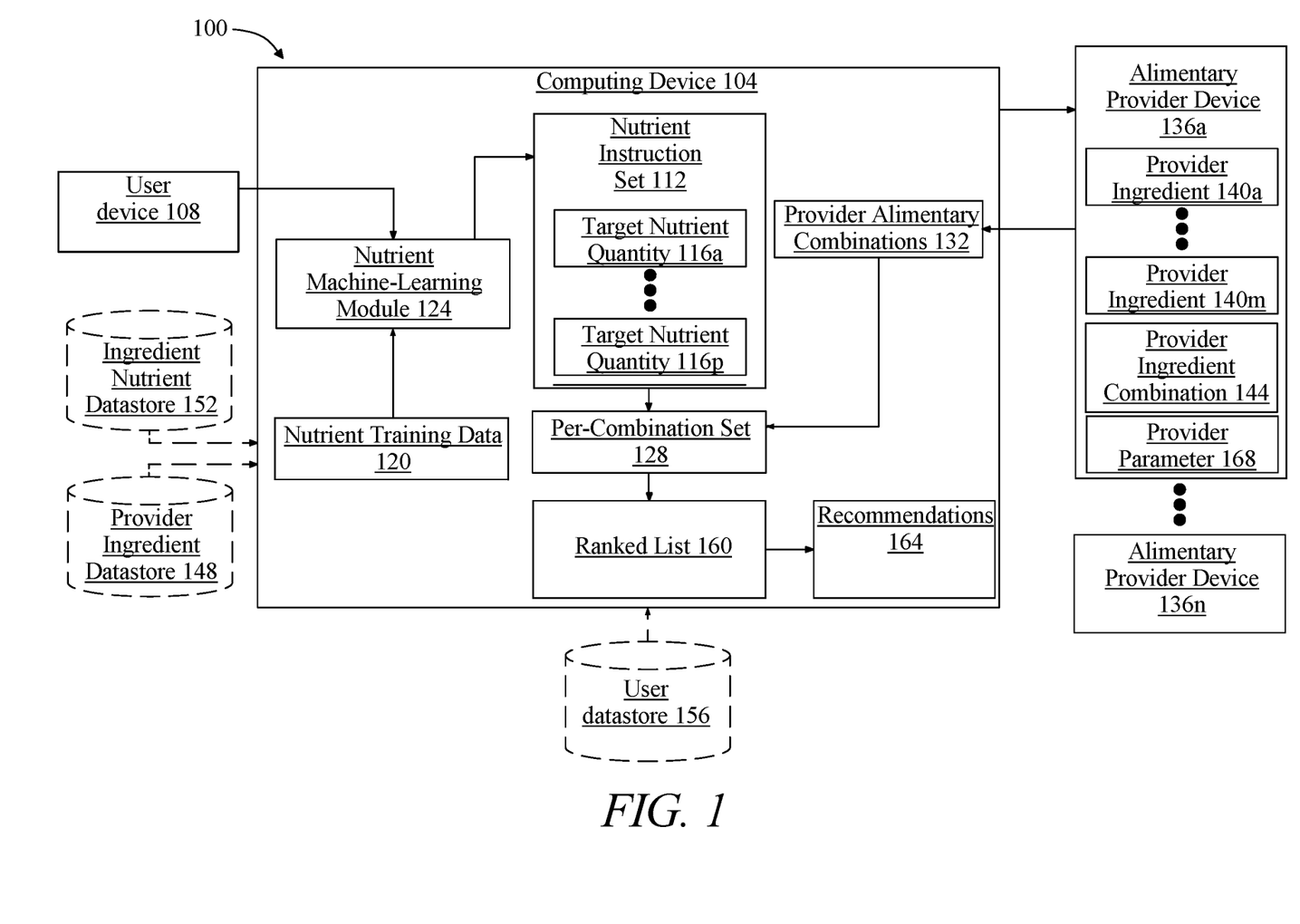
FIG. 1 is a block diagram illustrating a system for ranking alimentary combinations using machine learning.

Referring now to FIG. 1, an exemplary embodiment of a system 100 for a system for ranking alimentary combinations using machine learning is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive an affliction from a user device 108. As used in this disclosure "affliction" is any a list or other collection of ailments, including but not limited to physical, spiritual, and/or psychological ailments correlating to an impact on the user. For example one ailment that may be included is when a biological alteration occurs due to depression, as the body is either no longer producing or recognizing serotonin or dopamine. A user may enter an affliction indicating to the computing device 104 the ailment associated with the user. A user may enter one or more subsequent ailments indicating to the computing device 104 that one or more additional ailments are present. As a further example, computing device 104 may present a list of afflictions to user, from which user may select an affliction the user currently suffers from. List may be presented, without limitation, in rank order to user computing device 104 may receive user selection of a user ailment and select additional ailment as a function of the user selection. Alternatively or additionally, a highest-ranking affliction and/or a list of highest-ranking affliction may be presented to user for user to select or reject by way of a user entry; rejection of one affliction so displayed may cause computing device 104 to display a next highest-ranking affliction to user, which may be repeated iteratively until user selects a listed affliction and/or enters an affliction by other means. Computing device 104 may present additional ailments that the user may accept or reject based on the user selection or user input. For example a user may select or input an ailment of ischemic heart disease, whereby computing device may generate a list of additional ailments correlating to the initial ailment selected or inputted, such as high blood pressure. Additional ailments may be ranked according to the degree of correlation with the initial user input or selection, whereby computing device 104 may display to user a next highest-ranking affliction associated with the current user affliction. User selection of remaining correlated afflictions may then be accepted or rejected by the user. Receiving user affliction using user device 108, and/or ranking of afflictions, may be implemented, without limitation, as described in U.S. Nonprovisional application Ser. No. 16/890,686, filed on Jun. 2, 2020 and entitled "ARTIFICIAL INTELLIGENCE METHODS AND SYSTEMS FOR CONSTITUTIONAL ANALYSIS USING OBJECTIVE FUNCTIONS" the entirety of which is incorporated herein by reference.

Still referring to FIG. 1, computing device 104 is configured to generate a nutrient instruction set 112 including a plurality of target nutrient quantities 116*a-p* corresponding to a plurality of afflictions. As used in this disclosure a "nutrient instruction set" is a list or other collection of nutritional recommendations for a user, including recommendations of foods, nutrients, ingredients, and/or quantities thereof, that a user should consume to reduce the distance associated with an affliction. Nutrient instruction set includes a plurality of target nutrient quantities. As used in this disclosure, a "target nutrient quantity" is a quantity of a given nutrient that nutrient instruction set 112 recommends user to consume for amelioration of affliction over a subject period. As used in this disclosure, a "subject period" may consist of a set time period such as a day, a week, a month, and the like thereof. Quantities may include numbers representing a maximal amount to be consumed, a minimal amount to be consumed, and/or a precise amount that is determined to be ideal. A quantity may be zero for a nutrient that a user should not receive, and/or for a nutrient having no positive health benefit; for example, a user who has heart disease may be recommended a quantity of zero for trans fats, saturated fats, or the like thereof.

Figure 2:
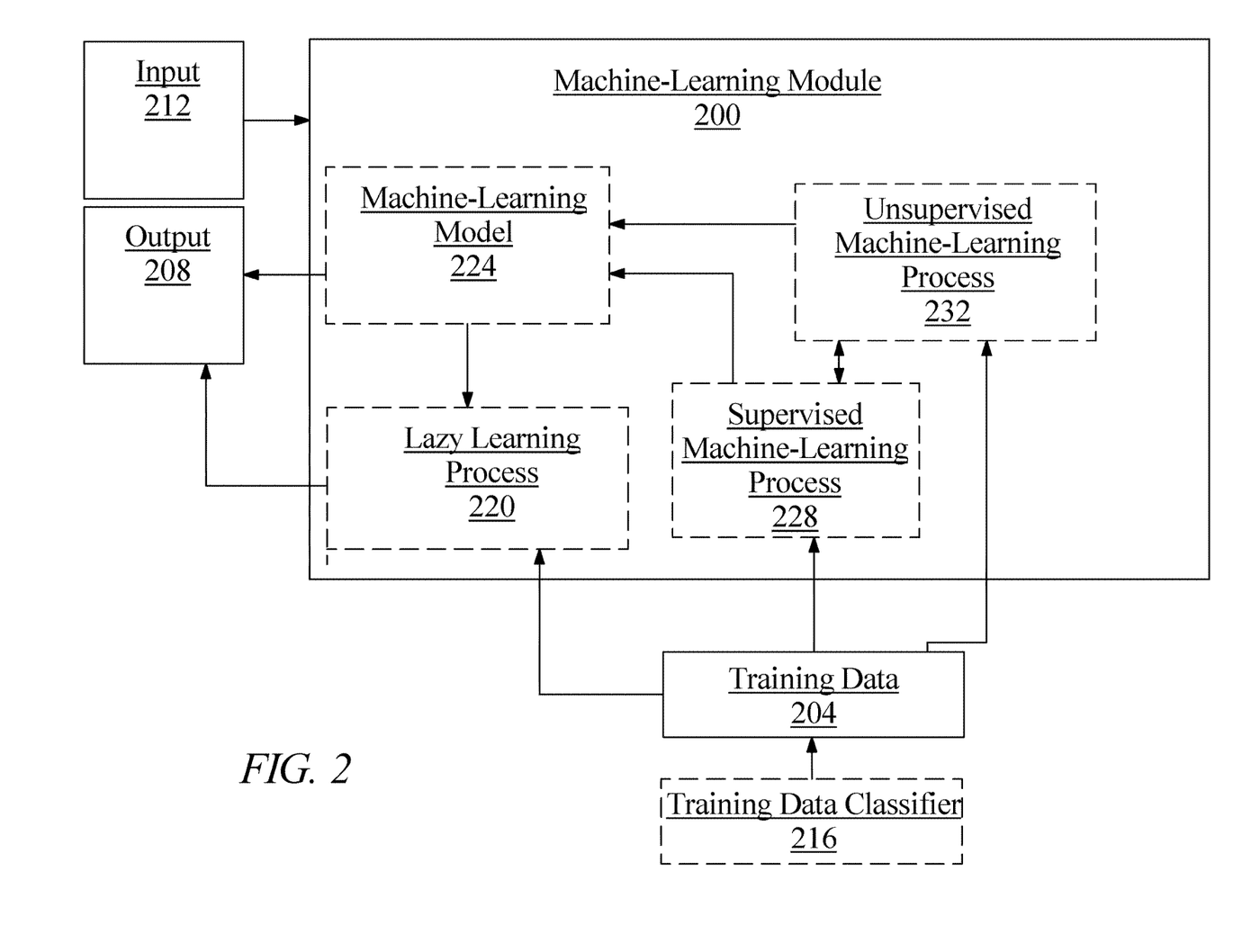
FIG. 2 is a block diagram of an exemplary embodiment of a machine-learning module.

With continued reference to FIG. 1, computing device 104 may generate nutrient instruction set 112 using a machine-learning process. Referring now to FIG. 2, an exemplary embodiment of a machine-learning module 200 that may perform one or more machine-learning processes as described in this disclosure is illustrated. Machine-learning module 200 may include any suitable machine-learning module may perform determinations, classification, and/or analysis steps, methods, processes, or the like as described in this disclosure using machine learning processes. A "machine learning process," as used in this disclosure, is a process that automatedly uses a training data 204 to generate an algorithm that will be performed by computing device 104/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device 104 and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to user cohorts, classes and/or categories of ingredient combinations, or the like.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An "unsupervised machine-learning process", as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods.

Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
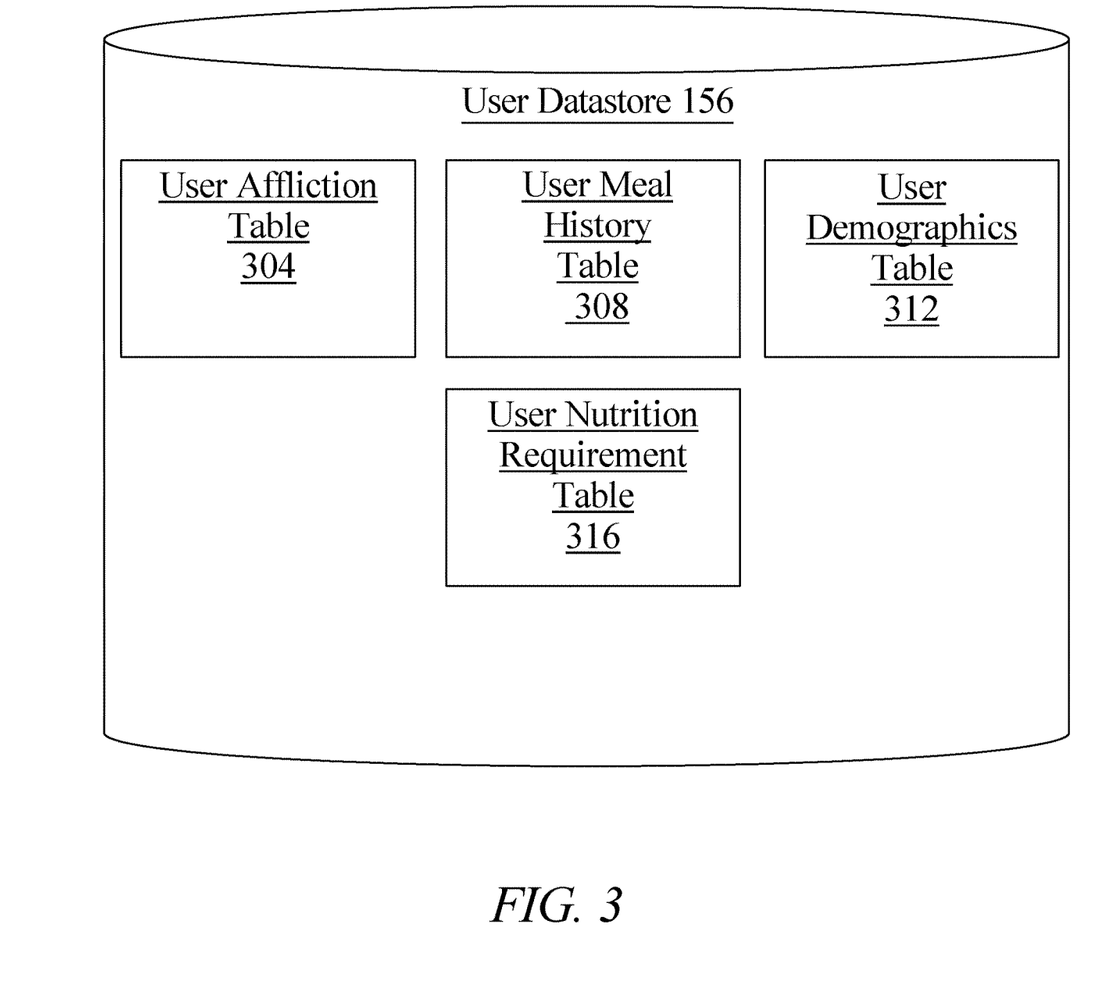
FIG. 3 is a block diagram of a user datastore according to an embodiment of the invention.

Referring now to FIG. 3, user datastore 156 may include a user affliction table 304, which may list afflictions and/or a combination of afflictions relating to the user. User datastore 108 may include a user meal history table 308, which may list past user meals that may have been stored. User datastore 108 may include a user demographic table 312, which may incorporate one more elements of demographic information relating to the user. This may include, without limitation, ethnicity, national origin, age, language, sex, geographic location of residence, or the like thereof. User datastore 108 may include a user nutrition requirement table 316, which may include previous nutrient targets relating to the user. Persons skilled in the art, upon reviewing the entirety of this disclosure, will be aware of various data that may be stored in user datastore 108 and/or tables in which data may be stored.

Still referring to FIG. 1, computing device 104 is configured to generate a list of afflictions. In an embodiment, computing device 104 may rank alimentary combinations using machine-learning includes computing device 104 configured to generate a ranked list 160 of afflictions, wherein generating further comprises receiving user constitutional data, classifying the constitutional data to a self-similar data cluster, and generating the list of afflictions as a function of the self-similar data cluster. For instance, and without limitation, a user may select a specific affliction, such as heart disease from the list of afflictions, whereby the system may then generate additional afflictions that the user may be experiencing. The system may then generate a further detailed target nutrient quantity 116 for the final user alimentary recommendation 164. Persons skilled in the art, upon reviewing the entirety of this disclosure, will be aware of various alternative or additional affliction target nutrients that may be used consistently with this disclosure.

Referring again to FIG. 1, computing device 104 may generate a nutrient instruction set 112, including a plurality of nutrient quantities set by receiving nutrient training data 120 correlating nutrient quantities to amelioration of afflictions, training a nutrient machine-learning model 124 as a function of nutrient training data 120, and generating nutrient instruction set 112 as a function of nutrient machine-learning model 124 and the affliction. Generation of nutrient instruction set 112 using machine learning may be implemented, without limitation, as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Alternatively or additionally, nutrient instruction set 112 may be received from user, from a medical professional, a nutritionist, and/or from one or more remote devices, including devices operated by user, by a medical professional, or the like thereof.

Still referring to FIG. 1, computing device 104 may determine a per-combination alimentary instruction set 128 as a function of nutrient instruction set 112. As used in this disclosure, a "per-combination alimentary instruction set" is an alimentary or plurality of alimentary as described above for nutrient instruction set 112. Per-combination alimentary instruction set 128 may be generated using any suitable process, including without limitation by dividing each target nutrient quantity of plurality of nutrient quantities by a number of planned alimentary combinations over a subject period.

With continued reference to FIG. 1, computing device 104 may receive a plurality of provider alimentary combinations 132 from each alimentary provider device 136 of a plurality of alimentary provider devices 136a-n. An alimentary provider device 136 may consist of one or more provider ingredient combinations 144, which may be defined for the purposes of this disclosure as a combination of provider ingredients 140a-m, which may be referred to as provider ingredients 140a-m that an alimentary provider and/or alimentary provider device 136 indicates may be provided, for instance and without limitation in the form of a meal package, prepared meal, meal kit, or the like. Alimentary provider device 136 may include any device suitable for use as computing device 104, as described above, which is operated by an alimentary provider. Provider alimentary combination 132 may include, without limitation a "meal package," defined as an ingredient combination to be prepared by an end user; preparation may include heating and/or reheating a cooked meal, combining ingredients, chopping ingredients, marinating ingredients, heating ingredients, boiling ingredients, and/or any other process of transforming ingredients into a meal. A meal package may come with instructions for preparation. A meal kit may instruct that users add water or other elements that may be external to meal package and/or provided by user.

Further referring to FIG. 1, an "alimentary provider," as used in this disclosure, is a person or entity that prepares alimentary products such as meals, food items, and/or drinks, including without limitation a restaurant, a food production service, a food delivery service, or the like. Provider ingredients 140a-m of provider ingredient combination 144 may include any ingredient or ingredients, where "ingredients" are defined as any ingredient in any alimentary product. In an embodiment, each alimentary provider device 136 may indicate a time period, such as a date range, during which each ingredient is available, a geographic region within which each ingredient is available, or the like; alternatively or additionally, each alimentary provider device 136 may solely indicate current availability of each ingredient and/or report only ingredients that are available from an alimentary provider associated with the alimentary provider device 136 at the time that transmission occurs. Computing device 104 may store received provider ingredients 140a-m in a provider ingredient datastore 148. Provider ingredient datastore 148 may include any data structure for ordered storage and retrieval of data, which may be implemented as a hardware or software module. Provider ingredient datastore 148 may be implemented, without limitation, as a relational database, a key-value retrieval datastore such as a NO SQL database, or any other format or structure for use as a datastore that a person skilled in the art would recognize as suitable upon review of the entirety of this disclosure. Provider ingredient datastore 148 may include a plurality of data entries and/or records as described above. Data entries in provider ingredient datastore 148 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in provider ingredient datastore 148 may reflect categories, cohorts, and/or populations of data consistently with this disclosure. Provider ingredient datastore 148 may be located in memory of computing device 104 and/or on another device in and/or in communication with system 100.

Referring again to FIG. 1, computing device 104 may group provider ingredients 140a-m within provider ingredient datastore 148 according to a geographical region in which the provider ingredients 140a-m are available, a time period during which the provider ingredients 140a-m are available, and/or any other category that may be defined by data associated with any provider ingredient 140 as described in this disclosure. Provider ingredients 140a-m may be grouped in provider ingredient datastore 148 according to identifiers of alimentary provider device 136a-n, and/or associated alimentary providers, that transmitted provider ingredients 140a-m; in other words, computing device 104 and/or other devices in and/or communicating with system 100 may be able to query provider ingredient datastore 148 using an identifier of an alimentary provider and receive in return a list of ingredients currently available to that provider and/or that will be available to that alimentary provider within a given time period and/or at a particular location.

Figure 4:
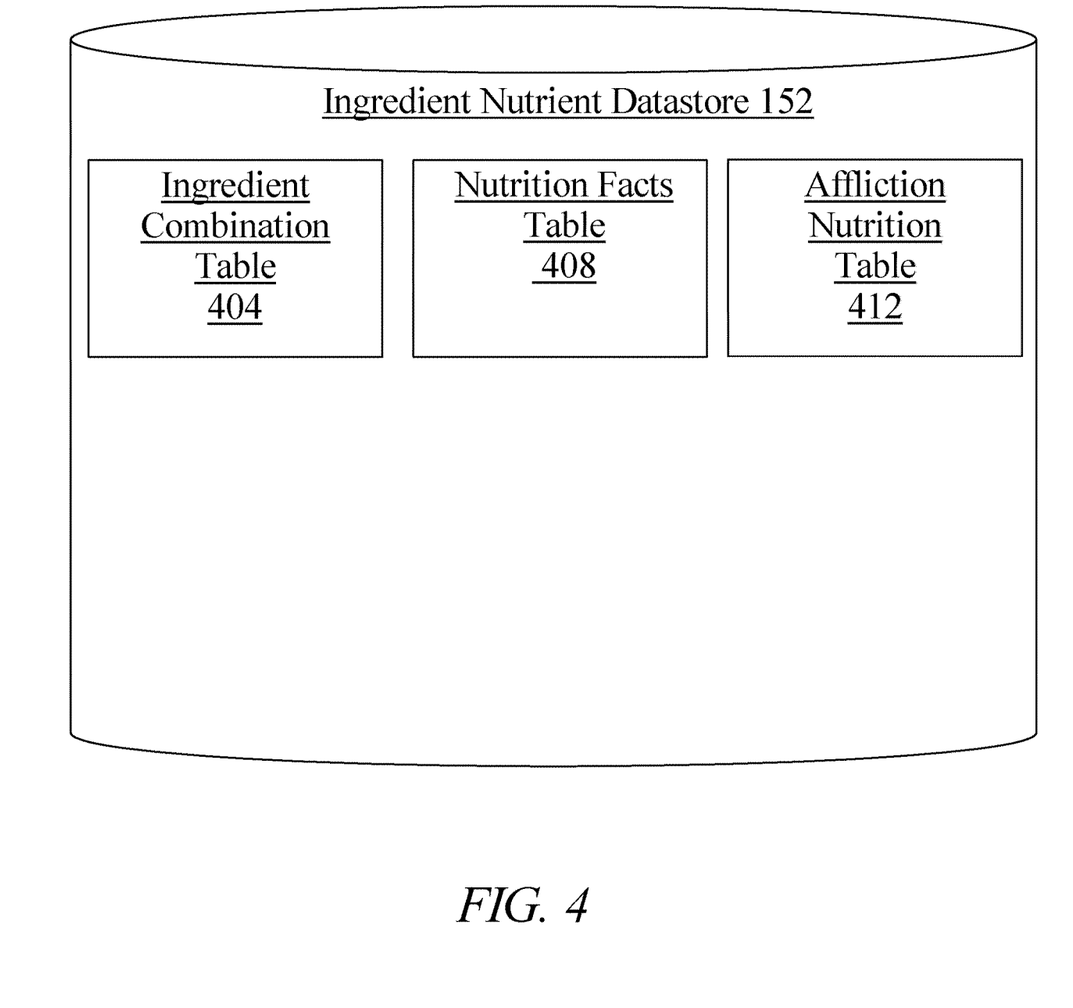
FIG. 4 is a block diagram of an ingredient nutrient datastore according to an embodiment of the invention.

Referring now to FIG. 4, ingredient nutrient datastore 152 may include an ingredient combination table 404, which may list ingredients used in each ingredient combination. Ingredient nutrient datastore 152 may include nutrition facts table 408, which may list nutrition quantities present in one or more ingredients and/or ingredient combinations; this may be used for comparison and distance and described in further detail herein. In this disclosure, "nutrition facts" may include protein, vitamin, and mineral classifiers and quantities. Ingredient nutrient datastore 152 may include an affliction nutrition table 412, which may indicate ingredients and/or ingredient combinations that are present in the ingredient for ameliorating afflictions.

Further referring to FIG. 1, computing device 104 is configured to generate a ranked list 160 of alimentary combinations by identifying a plurality of candidate alimentary combinations as a function of the plurality of alimentary combinations, or generating ranked list 160 as a function of the plurality of candidate alimentary combinations. A "ranked list," as used in this disclosure, is an ordered collection of data elements for which an order of presentation is defined according to ascending or descending values of a quantitative or other textual field associated with each element in the ordered collection. Computing device 104 may accomplish this, without limitation, by determining a nutrient listing corresponding to each ingredient combination of the plurality of provider ingredient combinations 144, for instance as retrieved from provider ingredient datastore 148.

Continuing to refer to FIG. 1, computing device 104 may generate ranked list by calculating a distance from the nutrient listing to nutrient instruction set 112 and selecting at least an ingredient listing that minimizes the distance to rank alimentary combinations according to a degree to which each minimizes the distance. This distance may be computed using any suitable distance metric. A "distance," as used in this disclosure, is a quantitative value indicating a degree of similarity of a set of data values to another set of data values. For instance, and without limitation, combinations of nutrient quantities associated with each alimentary combination, and target nutrient quantities 116 of nutrient instruction set 112, may be represented a vector. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting illustration, target nutrients from nutrient instruction set 112, and/or one or more subsets thereof, may be represented using a vector or other data structure, and nutrients provided by each alimentary combination of plurality of alimentary combinations may be represented by a like data structure, such as another vector; a distance comparing the two data structures may then be calculated and compared to distances calculations to find a minimal distance calculation and/or a set of minimal distance calculations. A set of minimal distance calculations may be a set of distance calculations less than a preconfigured threshold distance from data structure representing target nutrients. Preconfigured threshold may be set by one or more expert users and/or determined statistically, for instance by finding a top quartile and/or number of percentiles of proximity in a series of distance determinations over time for user, at one time for a plurality of users, and/or over time for a plurality of users. Plurality of users may include a plurality of users selected by a user classifier, which may classify user to a plurality of users having similar physiological data and/or user data; implementation of a user classifier may be performed, without limitation, as described in U.S. Nonprovisional application Ser. No. 16/865,740, filed on May 4, 2020 and entitled "METHODS AND SYSTEMS FOR SYSTEM FOR NUTRITIONAL RECOMMENDATION USING ARTIFICIAL INTELLIGENCE ANALYSIS OF IMMUNE IMPACTS," the entirety of which is incorporated herein by reference. In an embodiment, a distance may include a measurement of an optimization of one or more factors that include distance, price, quality and/or availability.

Still referring to FIG. 1, distance may be determined using a distance of, or in other words used in, a classifier as described above in reference to FIG. 2. A classifier used to compute distance may include, without limitation, a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements. KNN algorithm may operate according to any suitable distance, including without limitation vector similarity as described above.

With continued regards to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Näive Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, computing device 104 may be configured to filter plurality of provider ingredients 140a-m according to one or more goal parameters. For instance, computing device 104 may identify a plurality of provider ingredient combination 144 as a function of plurality provider ingredients 140a-m. Computing device 104 may then generate ranked list 160 as a function of plurality of provider alimentary combination 132, according to any process described above for generation of ranked list 160. Identifying plurality of recommended alimentary combinations 164 may include elimination of one or more provider alimentary combination 144 that diverge too greatly from nutrient instruction set 112. For instance, and without limitation, computing device 104 may compare a distance corresponding to each provider alimentary combination 132 to a preconfigured threshold, which may be any quantitative value representing a minimum, maximum, and/or range of acceptable distance values, and eliminate each ingredient combination that fails the threshold comparison, where "failing" indicates without limitation being less than a minimal threshold, more than a maximal threshold, and/or outside a range defined by a threshold. As a further non-limiting example, identifying plurality of provider alimentary combination 132 may include receiving at least a user parameter and identifying the plurality of alimentary combinations to match the at least a user affliction.

Within continued regard to FIG. 1, computing device 104 may be configured to generate a modified ranked list 160 by determining modified per-combination alimentary instruction set 128 and generating the modified ranked list 160 as a function of the modified per-combination alimentary instruction set 128. Generation of modified ranked list 160 may be performed using any method and/or method steps for generation of ranked list 160 as described above. Modified ranked list 160 may be generated using modified recommended nutrient quantities, where modification of nutrient quantities is performed as a function of selected alimentary combination. For instance, and without limitation, computing device 104 may determine modified per-combination alimentary instruction set 128 and generate modified ranked list 160 as a function of modified per-combination alimentary instruction set 128. As a non-limiting example, any nutrient quantities to be consumed in selected ingredient combination may be subtracted from nutrient quantities of alimentary instruction set, after which a new per-combination alimentary instruction set 128 may be determined as above. Persons skilled in the art, upon reviewing the entirety of this disclosure, will be aware of various ways in which per-combination alimentary instruction set 128 may be modified based on an alimentary combination selection.

In an embodiment, and further referring to FIG. 1, computing device 104 may be configured to display ranked list 160 and/or at least recommended alimentary combination 164 to the user. Computing device 104 may receive a user selection of an ingredient combination, for instance by way of user selection of a link, button and/or other display element corresponding to a recommended alimentary combination 164. Computing device 104 may automatically initiate preparation and/or delivery of selected ingredient combination, for instance and without limitation by transmitting indication of selection to a corresponding alimentary provider device 136.

With continued reference to FIG. 1, computing device 104 may perform machine-learning algorithms using a loss function analysis to select each recommended alimentary combination 164 from plurality of candidate alimentary combinations. In an embodiment, computing device 104 may compare one or more user specific inputs to a mathematical expression representing a plurality of goal parameters. Mathematical expression may include a linear combination of variables, weighted by coefficients representing relative importance of each goal parameter. For instance, a variable such as food quality, importance to user of organic ingredients versus nonorganic ingredients may be multiplied by a first coefficient representing the importance of organic food standards, a second user input such as total cost may be multiplied by a second coefficient representing the importance of cost, a degree of variance from a and/or classified beneficial ingredient set may be represented as another parameter, which may be multiplied by another coefficient representing the importance of that parameter, a degree of variance from a preference for fresh or frozen ingredients may be multiplied by an additional coefficient representing an importance of that parameter, or the like; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, computing device 104 may calculate variables of set of provider parameters 168 and/or variance of such parameters from goal parameters calculate an output of mathematical expression using the variables, and select candidate alimentary combination that produces an output having the lowest size, according to a given definition of "size," of the set of outputs representing each of plurality of candidate alimentary combinations; size may, for instance, included absolute value, numerical size, or the like. Selection of different loss functions may result in identification of different candidate alimentary combinations as generating minimal outputs; for instance, where organic ingredients is associated in a first loss function with a large coefficient or weight, a candidate alimentary combination having a small coefficient or weight for organic ingredients may minimize the first loss function, whereas a second loss function wherein organic ingredients has a smaller coefficient but degree of variance from cost goal which has a larger coefficient may produce a minimal output for a different candidate alimentary combination having a larger organic ingredients but more closely hewing to a cost goal.

Alternatively or additionally, and still referring to FIG. 1, each alimentary combination and/or provider alimentary combination 132 may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each parameter. A provider alimentary combination 132 and/or provider ingredient combination 144 having a mathematical expression minimizing the error function may be selected, as representing an optimal expression of relative importance of parameters to a system or user. In an embodiment, error function and loss function calculations may be combined; for instance, a provider alimentary combination 132 and/or provider ingredient combination 144 resulting in a minimal aggregate expression of error function and loss function, such as a simple addition, arithmetic mean, or the like of the error function with the loss function, may be selected, corresponding to an option that minimizes total variance from goal parameters while simultaneously minimizing a degree of variance from a set of priorities corresponding to goal parameters. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each parameter to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function, such as without limitation using a regression algorithm. Mathematical expression and/or loss function may be user-specific, using a training set composed of past user selections; mathematical expression and/or loss function may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary combinations 148. Use of regression to derive loss functions, loss function coefficients, and/or mathematical expressions may be performed, without limitation, as described in U.S. Nonprovisional application Ser. No. 16/502,835.

Still referring to FIG. 1, in an embodiment, steps described above may be performed iteratively; at each iteration user may select one or more alimentary combinations, upon which computing device 104 may regenerate rankings, display regenerated rankings, generate recommended alimentary combination 164, and/or display recommended alimentary combinations 164. Iteration may be repeated until an affliction as described above has been ameliorated with user selections. Recommended alimentary combinations 164 may be displayed concurrently with ranked list 160, for instance and without limitation in separate windows, frames, or the like, permitting user to select recommended alimentary combination 164, ingredient combinations from ranked list 160, or the like thereof. Upon presentation with a recommended alimentary combination 164, user may accept entire recommended alimentary combination, accept a subset thereof while rejecting a remainder thereof, accept one or more while selecting another alimentary from ranked list 160, or rejecting all recommended alimentary combinations 164 and selecting one or more other edibles from ranked list 160.

Figure 5:
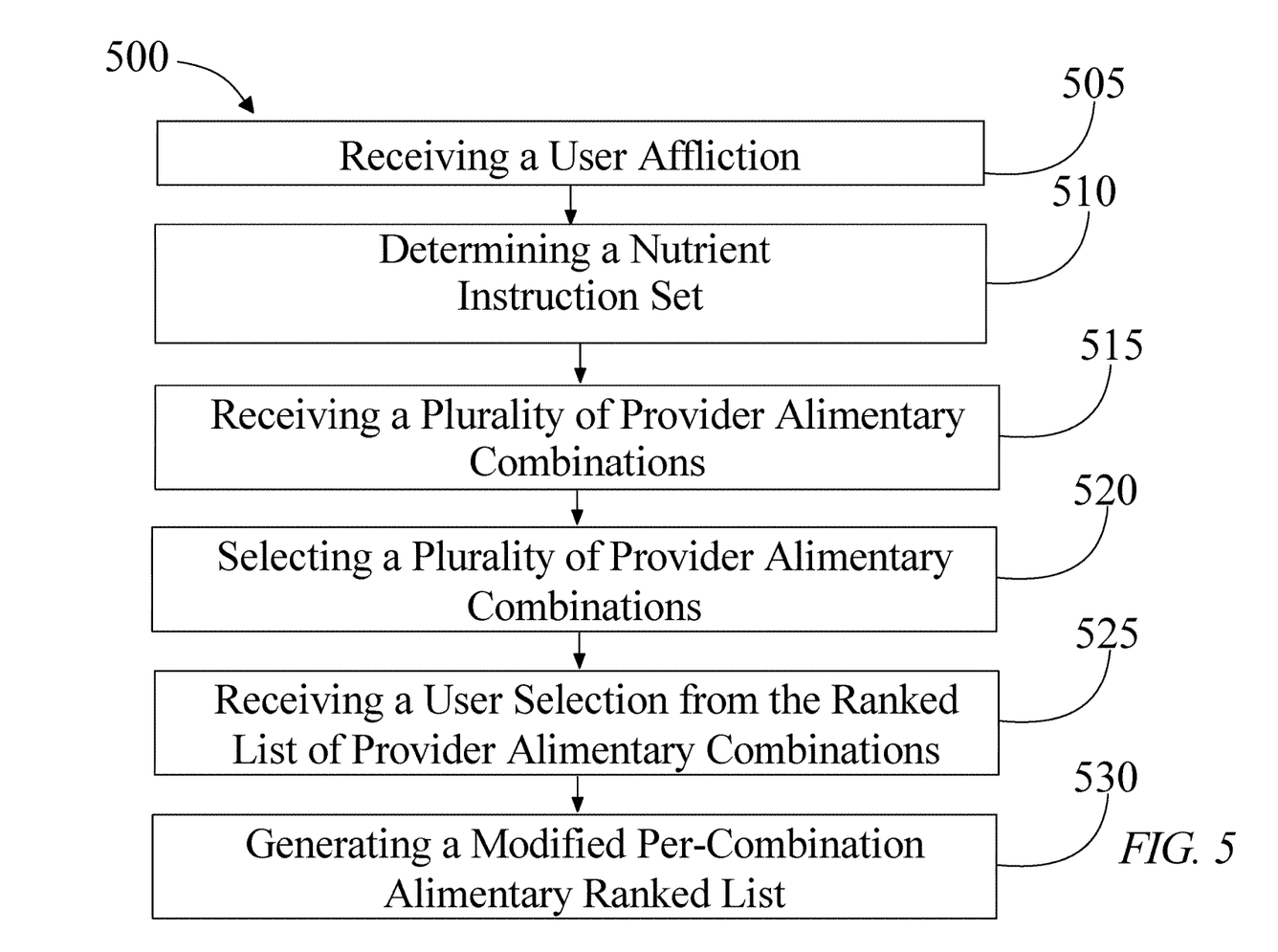
FIG. 5 is a flow diagram illustrating an exemplary method of ranking alimentary combinations using machine learning.

Referring now to FIG. 5, an exemplary embodiment of a method 500 of ranking alimentary combinations using machine-learning is illustrated. At step 505, computing device 104 receives from user device 108 a user affliction including a plurality of user afflictions; this may be implemented, without limitation, as described above in reference to FIGS. 1-4.

At step 510, and still referring to FIG. 5, computing device 104 determines a nutrient instruction set 112 as a function of the plurality of target nutrient quantities 116; this may be implemented, without limitation, as described above in reference to FIGS. 1-4. Providing nutrient instruction set 112 may include receiving nutrient training data 120, training nutrient machine-learning model 124 as a function of nutrient training data 120, and generating the at least nutrient instruction set 112 as a function of the nutrient machine-learning model 124 and the user affliction, for instance as described above.

At step 515, and with continued reference to FIG. 5, computing device 104 receives from each alimentary provider device 136 of a plurality of alimentary provider device 136a-n, a plurality of provider alimentary combination 132; this may be implemented, without limitation, as described above in reference to FIGS. 1-4.

At step 520, and still referring to FIG. 5, computing device 104 generates ranked list 160 of alimentary combinations as a function of the plurality of provider alimentary combination 132; this may be implemented, without limitation, as described above in reference to FIGS. 1-4. Selecting each alimentary combination of the plurality of beneficial alimentary combinations includes determining a nutrient listing corresponding to each alimentary combination of the plurality of provider alimentary combination 132, calculating a distance from the nutrient listing to the per-combination alimentary instruction set 128, and selecting at least an nutrient listing that minimizes the distance, and ranking the plurality provider alimentary combination 132 to minimize the distance. Generating the ranked list 160 of alimentary combinations may include identifying a plurality of candidate alimentary combinations as a function of the plurality ingredients and generating ranked list 160 as a function of the plurality of candidate alimentary combinations. Identifying the plurality of candidate alimentary combinations may include comparing, for each provider ingredient combination of the plurality of provider alimentary combinations 132, a distance corresponding to the provider ingredient combinations to a preconfigured threshold, and eliminating each provider ingredient combination that fails the threshold comparison Identifying the plurality of candidate alimentary combinations may include receiving at least a user parameter and identifying the plurality of candidate alimentary combinations to match the at least a user parameter. Calculating distance may include generating requirement ingredients corresponding to target nutrition quantities and calculating the distance from provider alimentary combinations 132 to affliction nutrient requirements. Calculating distance may include calculating a classifier distance.

At step 525, and further referring to FIG. 5, computing device 104 receives a user selection of provider alimentary combination 132 corresponding to a meal of the plurality of affliction target nutrients; this may be implemented, without limitation, as described above in reference to FIGS. 1-4. Receiving user selection may include displaying ranked list 160 on a user client device and receiving a user selection of the displayed ranked list 160.

At step 530, and still referring to FIG. 5, computing device 104 generates modified ranked list 160 of alimentary combinations as a function of user selection and nutrient instruction set 112; this may be implemented, without limitation, as described above in reference to FIGS. 1-4. Generating modified ranked list 160 may include determining a modified per-combination alimentary instruction set 128 and generating the modified ranked list 160 as a function of the modified per-combination alimentary instruction set 128.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 6:
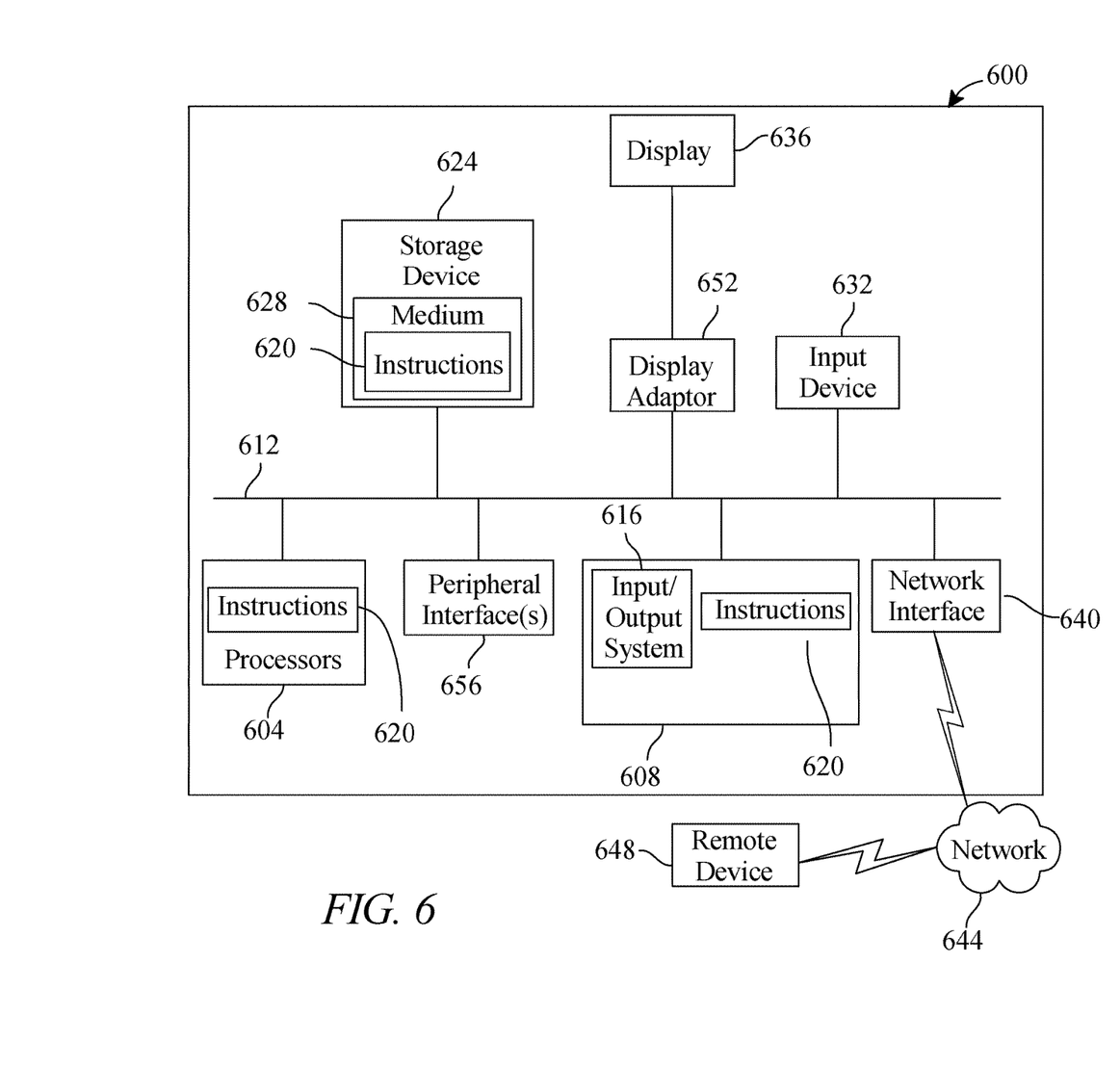
FIG. 6 is a block diagram of a computing system that can be used to implement any one or more of the methodologies disclosed herein and any one or more portions thereof.

FIG. 6 shows a diagrammatic representation of one embodiment of computing device 104 in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104s, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for ranking alimentary combinations using machine learning, the system comprising:
   a computing device, the computing device configured to:
      receive, from a user device, an affliction relating to a user of the user device;
      generate a nutrient instruction set including a plurality of nutrient quantities, wherein each nutrient quantity in the plurality of nutrient quantities is associated with a subject period, wherein generating the nutrient instruction set further comprises:
         receiving nutrient training data correlating nutrient quantities to amelioration of afflictions;
         training a nutrient machine-learning model as a function of the nutrient training data; and
         generating the nutrient instruction set as a function of the nutrient machine-learning model and the affliction;
      derive, as a function of the nutrient instruction set and at least the subject period, a per-combination alimentary instruction set;
      receive, from each alimentary provider device of a plurality of alimentary provider devices, a plurality of provider alimentary combinations;
      generate a ranked list of alimentary combinations as a function of the plurality of provider alimentary combinations and the per-combination alimentary instruction set, wherein generating the ranked list of alimentary combinations comprises:
         determining a nutrient list corresponding to each alimentary combination of the plurality of provider alimentary combinations;
         calculating a distance from the nutrient list to the per-combination alimentary instruction set, wherein the distance comprises a degree of similarity between a vector representing the nutrient list and another vector representing the per-combination alimentary instruction set; and
         selecting at least an alimentary list that minimizes the distance;
      identify at least a recommended alimentary combination as a function of the plurality of provider alimentary combinations and the nutrient instruction set, wherein identifying the at least a recommended alimentary combination comprises:
         determining a provider ingredient combination for each provider alimentary combination from the plurality of provider alimentary combinations;
         calculating a provider distance from each provider ingredient combination to the nutrient instruction set;
         comparing the provider distance for each provider alimentary combination to a preconfigured threshold, wherein the preconfigured threshold is set by finding a top quartile of proximity in a series of distance determinations over time, and wherein the series of distance determinations are quantitative values indicating a degree of similarity between the provider distance for each provider alimentary combination to the preconfigured threshold; and
         identifying the at least a recommended alimentary combination as a function of the calculated provider distance and the comparison of each provider alimentary combination to the preconfigured threshold; and
      display the ranked list and the at least a recommended alimentary combination on the user device.

2. The system of claim 1, wherein the computing device is further configured to receive the affliction by:
   generating a list of afflictions on the user device; and
   utilizing a user selection from the list of afflictions.

3. The system of claim 2 wherein generating the list of afflictions further comprises:
   receiving user constitutional data;
   classifying the constitutional data to a self-similar data cluster; and
   generating the list of afflictions as a function of the self-similar data cluster.

4. The system of claim 1, wherein the computing device is further configured to generate the ranked list of alimentary combinations by:
   identifying a plurality of candidate alimentary combinations as a function of the plurality of provider alimentary combinations; and
   generating the ranked list as a function of the plurality of candidate alimentary combinations.

5. The system of claim 1, wherein calculating the distance further comprises calculating the distance using a classifier.

6. The system of claim 5, wherein the classifier is a k-nearest neighbors classifier.

7. The system of claim 5, wherein the classifier is a naïve Bayes classifier.

8. The system of claim 1 wherein the computing device is further configured to:
   receive an identification of an alimentary combination from the ranked list; and
   generate a modified ranked list.

9. The system of claim 8, wherein the computing device is configured to generate the modified ranked list by:
   determining a modified per-combination alimentary instruction set; and generate the modified ranked list as a function of the modified per-combination alimentary instruction set.

10. A method for ranking alimentary combinations using machine learning, the method comprising:
receiving, by a computing device, an affliction relating to a user;
generating, by the computing device, a nutrient instruction set including a plurality of nutrient quantities, wherein each nutrient quantity in the plurality of nutrient quantities is associated with a subject period, wherein generating the nutrient instruction set further comprises:
retrieving nutrient training data correlating nutrient quantities to amelioration of afflictions;
training a nutrient machine-learning model as a function of the nutrient training data; and
generating the nutrient instruction set as a function of the nutrient machine-learning model and the affliction;
deriving, by the computing device, as a function of the nutrient instruction set and at least the subject period, a per-combination alimentary instruction set;
receiving, by the computing device, from each alimentary provider computing device of a plurality of alimentary provider computing devices, a plurality of provider alimentary combinations;
generating, by the computing device, a ranked list of alimentary combinations as a function of the plurality of provider alimentary combinations and the per-combination alimentary instruction set, wherein generating the ranked list of alimentary combinations comprises:
determining a nutrient list corresponding to each alimentary combination of the plurality of provider alimentary combinations;
calculating a distance from the nutrient list to the per-combination alimentary instruction set, wherein the distance comprises a degree of similarity between a vector representing the nutrient list and another vector representing the per-combination alimentary instruction set; and
selecting at least an alimentary list that minimizes the distance; and
identifying, by the computing device, at least a recommended alimentary combination as a function of the plurality of provider alimentary combinations and the nutrient instruction set, wherein identifying the at least a recommended alimentary combination comprises:
determining a provider ingredient combination for each provider alimentary combination from the plurality of provider alimentary combinations;
calculating a provider distance from each provider ingredient combination to the nutrient instruction set;
comparing the provider distance for each provider alimentary combination to a preconfigured threshold, wherein the preconfigured threshold is set by finding a top quartile of proximity in a series of distance determinations over time, and wherein the series of distance determinations are quantitative values indicating a degree of similarity between the provider distance for each provider alimentary combination to the preconfigured threshold; and
identifying the at least a recommended alimentary combination as a function of the calculated provider distance and the comparison of each provider alimentary combination to the preconfigured threshold; and
displaying, by the computing device, the ranked list and the at least a recommended alimentary combination on a display device.

11. The method of claim 10, wherein receiving the affliction further comprises:
generating a list of afflictions on a user device; and
utilizing a user selection from the list of afflictions.

12. The method of claim 11, wherein generating the list of afflictions further comprises:
receiving user constitutional data;
classifying the constitutional data to a self-similar data cluster; and
generating the list of afflictions as a function of the self-similar data cluster.

13. The method of claim 10, wherein generating the ranked list of alimentary combinations further comprises:
identifying a plurality of candidate alimentary combinations as a function of the plurality of provider alimentary combinations; and
generating the ranked list as a function of the plurality of candidate alimentary combinations.

14. The method of claim 10, wherein calculating the distance further comprises calculating the distance using a classifier.

15. The method of claim 14, wherein the classifier is a k-nearest neighbors classifier.

16. The method of claim 14, wherein the classifier is a naïve Bayes classifier.

17. The method of claim 10, further comprising receiving an identification of an alimentary combination from the ranked list; and generating a modified ranked list.

18. The method of claim 17, wherein generating the modified ranked list further comprises:
determining a modified per-combination alimentary instruction set; and
generate the modified ranked list as a function of the modified per-combination alimentary instruction set.

* * * * *